(12) United States Patent
Anson

(10) Patent No.: US 11,464,663 B1
(45) Date of Patent: Oct. 11, 2022

(54) LUMBAR THERAPY BELT

(71) Applicant: David Anson, Pompton Plains, NJ (US)

(72) Inventor: David Anson, Pompton Plains, NJ (US)

( * ) Notice: Subject to any disclaimer, the term of this patent is extended or adjusted under 35 U.S.C. 154(b) by 675 days.

(21) Appl. No.: 16/512,528

(22) Filed: Jul. 16, 2019

(51) Int. Cl.
*A61F 5/02* (2006.01)
*A61F 5/042* (2006.01)
*A61F 5/34* (2006.01)
*A61H 1/02* (2006.01)

(52) U.S. Cl.
CPC .............. *A61F 5/028* (2013.01); *A61F 5/042* (2013.01); *A61F 5/34* (2013.01); *A61H 1/0292* (2013.01); *A61H 2201/163* (2013.01)

(58) Field of Classification Search
CPC .. A61F 5/028; A61F 5/02; A61F 5/026; A61F 5/03; A61F 5/024; A61F 2250/001; A61F 5/01; A61F 5/30; A61F 5/022; A61F 5/058; A61F 2210/0076; A61F 5/0102; A61F 5/0193; A61F 2005/0155; A61F 5/0104; A61F 5/34; A61F 13/00038; A61F 13/145; A61F 2005/0183; A61F 2005/0197; A61F 2007/0024; A61F 2007/0228; A61F 2007/0231; A61F 5/3715; A61F 5/3784; A61F 9/002; A61F 9/025; A61F 9/00; A61F 9/02; A61F 19/00; A61F 1/00; A61F 11/16; A61F 17/02; A61F 9/007; A41F 9/002; A41F 9/025; A41F 9/00; A41F 9/02; A41F 19/00; A41F 1/00; A41F 11/16; A41F 17/02; A41F 9/007; A45F 2003/045
See application file for complete search history.

(56) References Cited

U.S. PATENT DOCUMENTS

| | | | |
|---|---|---|---|
| 1,182,592 A * | 5/1916 | Smyth | A61F 5/26 128/105.1 |
| 5,122,111 A | 6/1992 | Sebastian | |
| 5,445,647 A | 8/1995 | Choy | |
| 5,470,304 A | 11/1995 | Decanto | |
| 5,551,085 A * | 9/1996 | Leighton | A61F 5/028 602/19 |
| 6,352,074 B1 | 3/2002 | Okada | |
| 6,711,750 B1 | 3/2004 | Too | |
| D638,949 S | 5/2011 | Martinez | |
| 2007/0299368 A1 | 12/2007 | McCarthy | |
| 2010/0121240 A1 * | 5/2010 | Smith | A61F 5/026 602/19 |
| 2017/0266030 A1 | 9/2017 | Hess | |

* cited by examiner

*Primary Examiner* — Ophelia A Hawthorne
(74) *Attorney, Agent, or Firm* — Kyle A. Fletcher, Esq.

(57) ABSTRACT

The lumbar therapy belt is a therapeutic device. The lumbar therapy belt is configured for use with a patient. The patient is further defined with a torso, a spine, a pelvis, an abdomen, and a lumbar region. The lumbar therapy belt includes a belt, a fastener, and a plurality of pads. The fastener and the plurality of pads attach to the belt. The belt is a strap. The fastener attaches the belt to the patient such that the plurality of pads are positioned over the lumbar region. The plurality of pads press against the lumbar region such that the normal movement of the patient causes the plurality of pads to stretch the muscles of the lumbar region, including spinal muscles, laterally so as to relieve downward pressure on the spinal discs and nerves.

19 Claims, 4 Drawing Sheets

LUMBAR THERAPY BELT

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

Field of the Invention

The present invention relates to the field of medical science including physical therapy apparatus, more specifically, a device for laterally diverting muscles and nerves to redistribute pressure exerted on spinal discs and nerves to the pelvis and legs without substantial movement between the skin and the device.

SUMMARY OF INVENTION

The lumbar therapy belt is a therapeutic device. The lumbar therapy belt is configured for use with a patient. The patient is further defined with a torso, a spine, a pelvis, an abdomen, and a lumbar region. The lumbar therapy belt is adapted to redistribute superior to inferior pressure in spinal discs and nerves laterally away from the lumbar region. The lumbar therapy belt comprises a belt, a fastener, and a plurality of pads. The fastener and the plurality of pads attach to the belt. The belt is a strap. The fastener attaches the belt to the patient such that the plurality of pads are positioned over the lumbar region. The plurality of pads press against the lumbar region such that the normal movement of the patient causes the plurality of pads to stretch the muscles of the lumbar region, including spinal muscles, laterally so as to relieve downward pressure on the spinal discs and nerves.

These together with additional objects, features and advantages of the lumbar therapy belt will be readily apparent to those of ordinary skill in the art upon reading the following detailed description of the presently preferred, but nonetheless illustrative, embodiments when taken in conjunction with the accompanying drawings.

In this respect, before explaining the current embodiments of the lumbar therapy belt in detail, it is to be understood that the lumbar therapy belt is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the lumbar therapy belt.

It is therefore important that the claims be regarded as including such equivalent construction insofar as they do not depart from the spirit and scope of the lumbar therapy belt. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
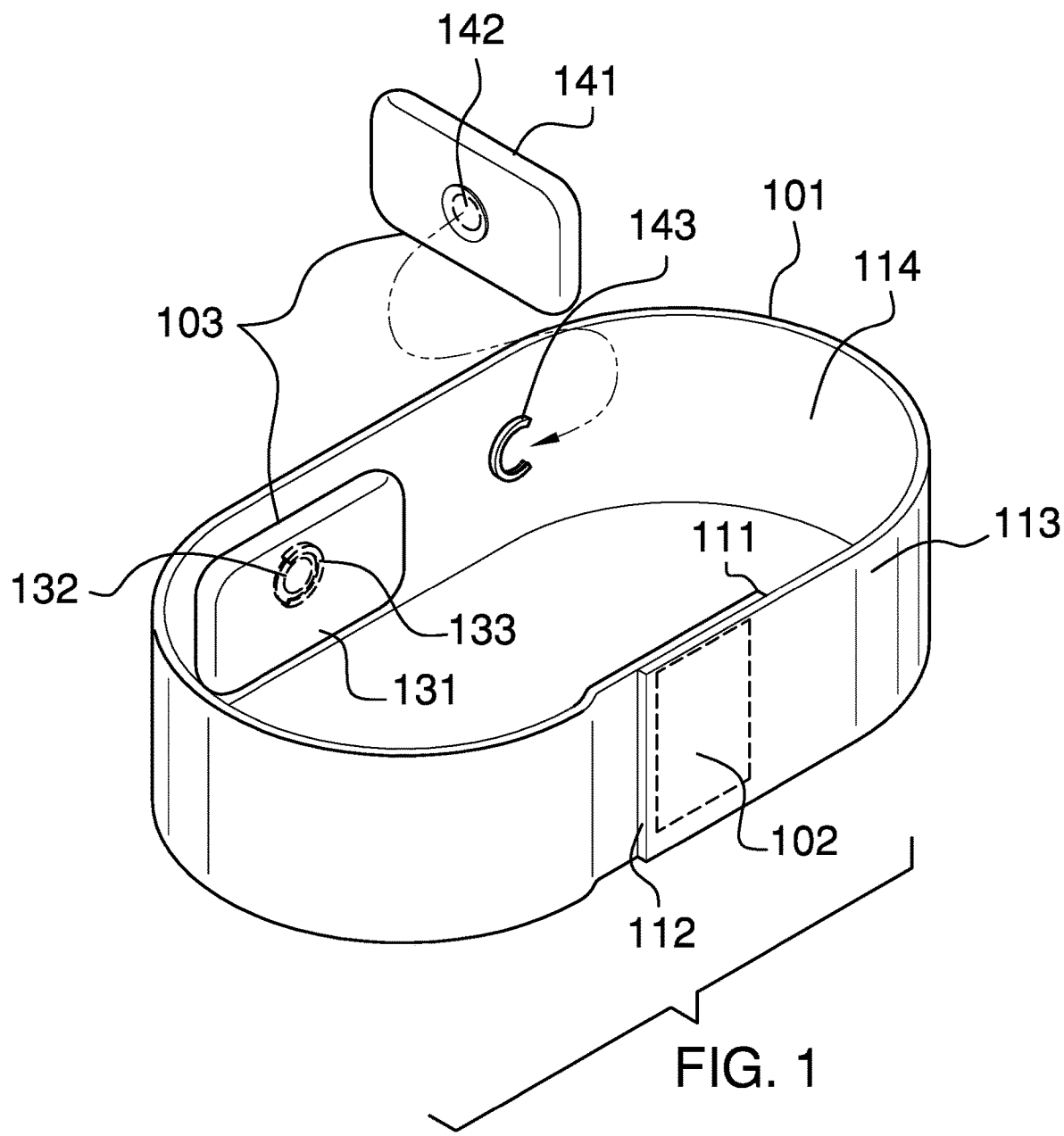
FIG. 1 is a perspective view of an embodiment of the disclosure.
Figure 2:
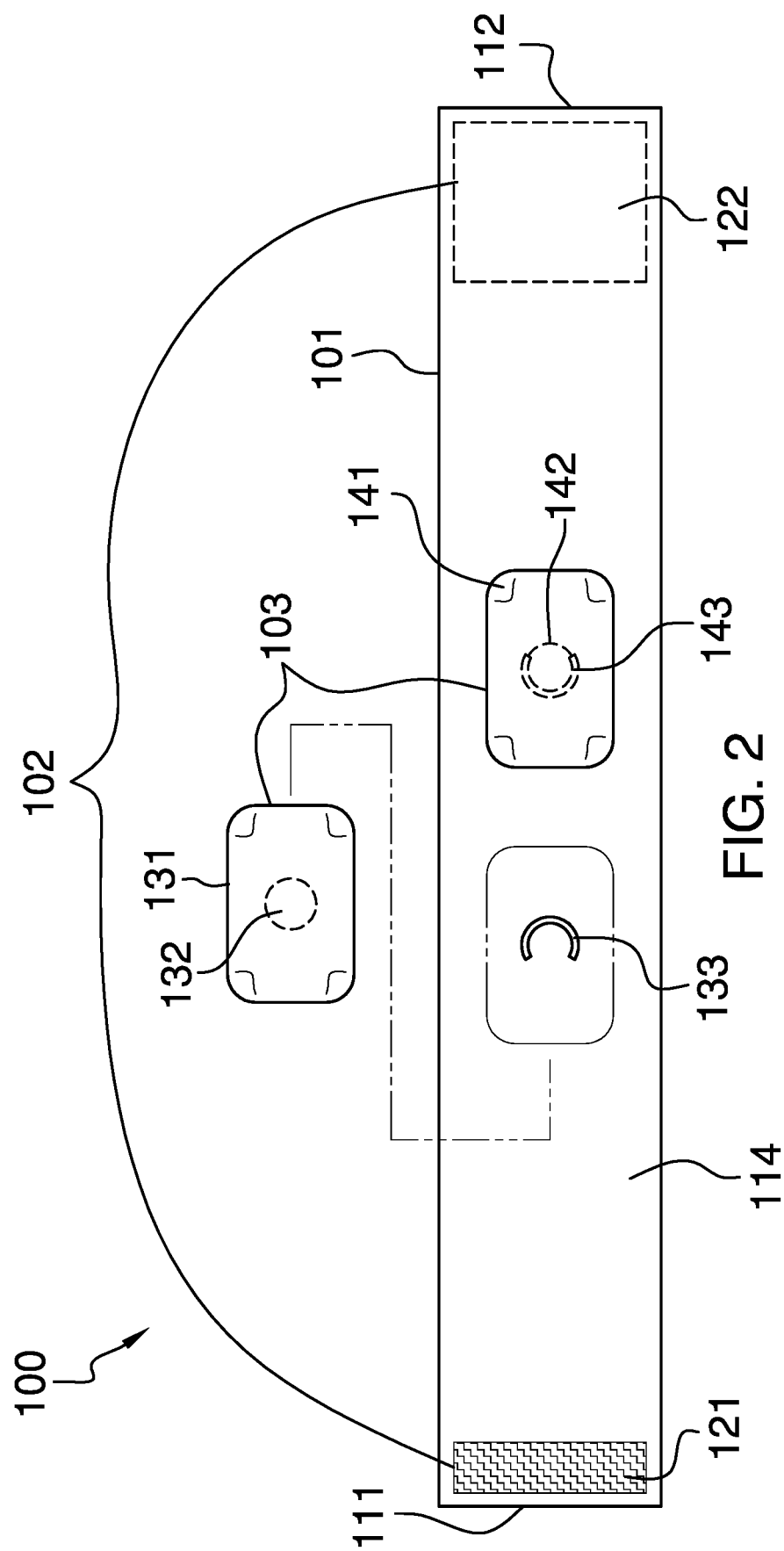
FIG. 2 is a front view of an embodiment of the disclosure.
Figure 3:
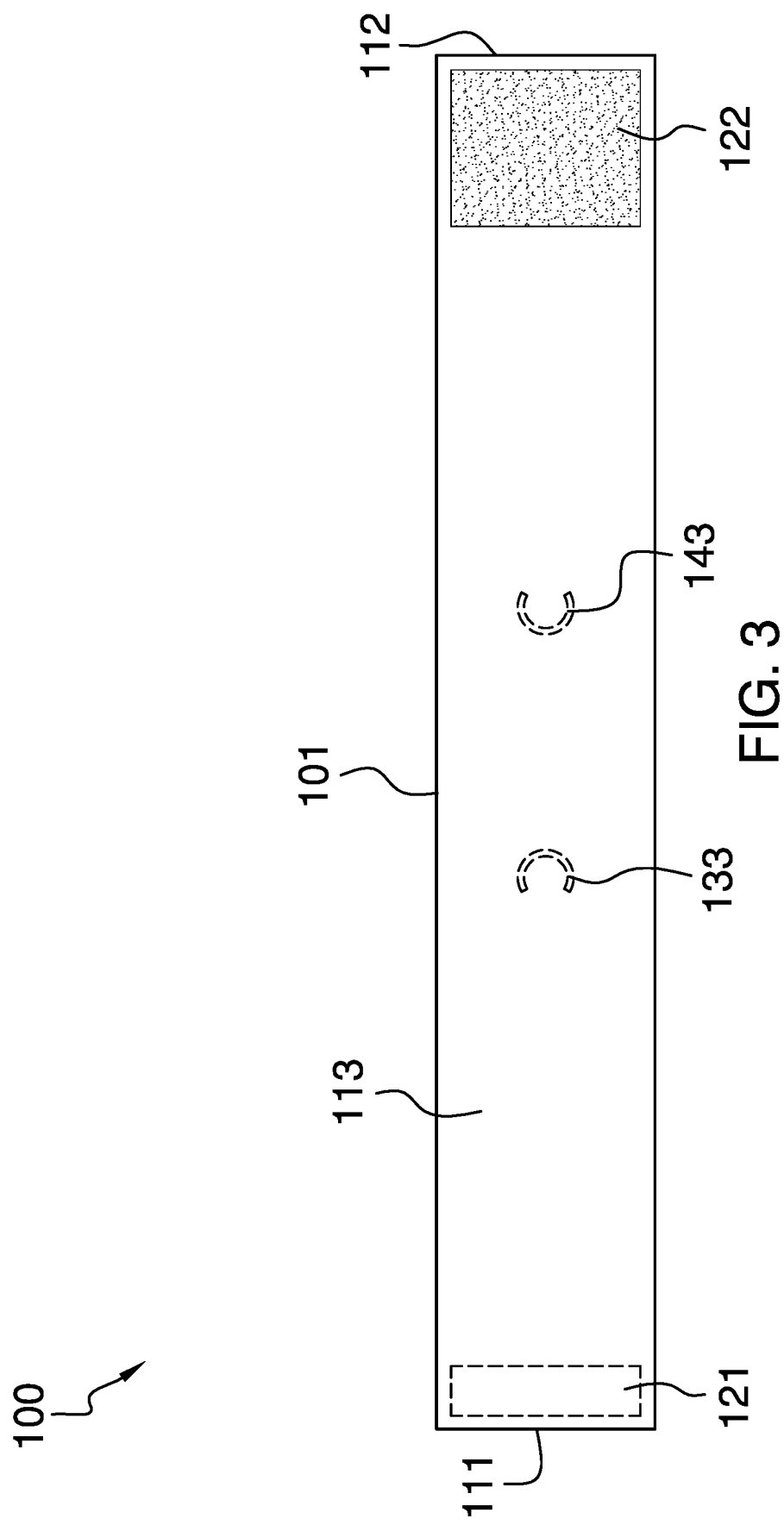
FIG. 3 is a rear view of an embodiment of the disclosure.
Figure 4:
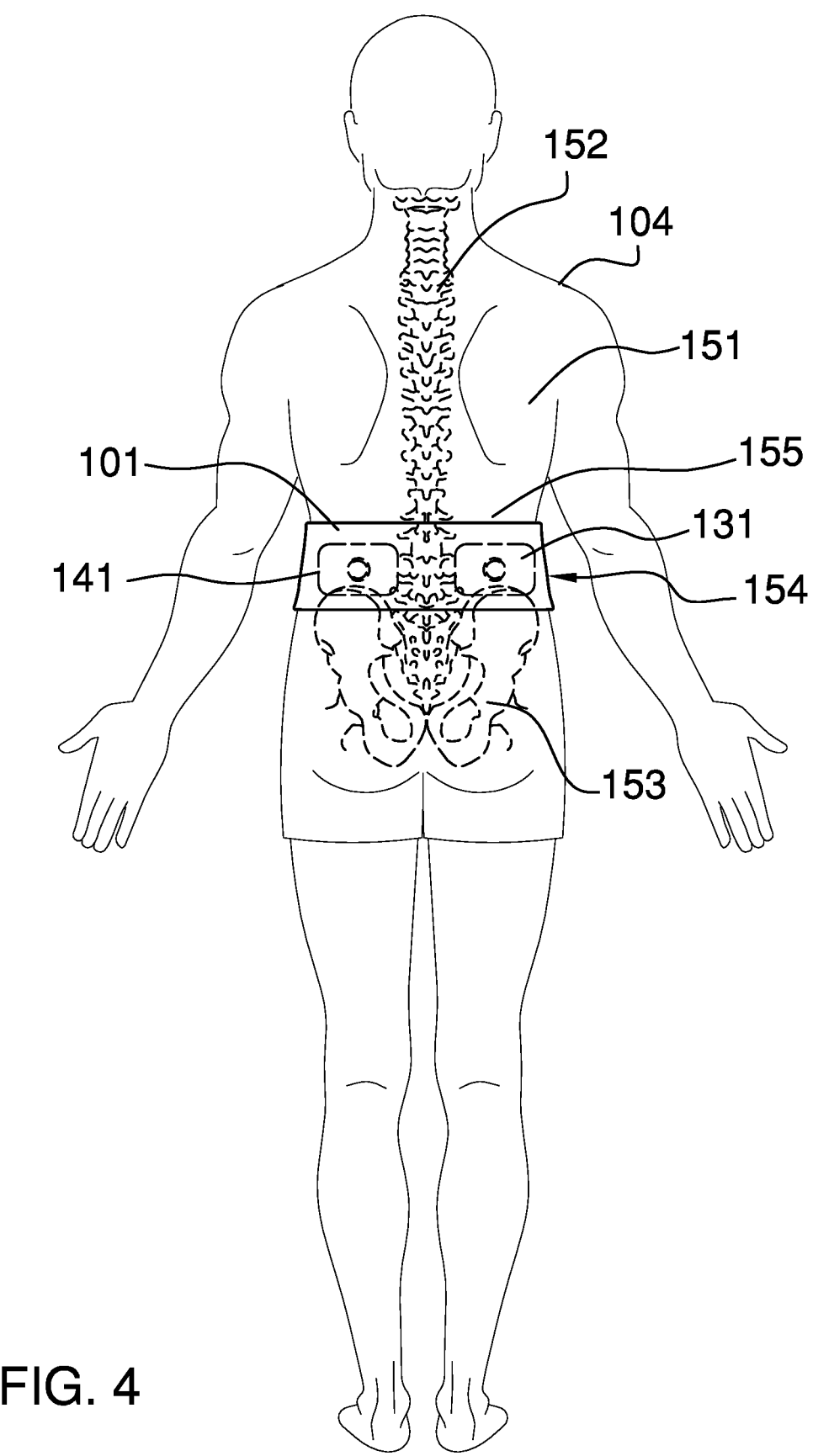
FIG. 4 is an in-use view of an embodiment of the disclosure.

Detailed reference will now be made to one or more potential embodiments of the disclosure, which are illustrated in FIGS. 1 through 4.

The lumbar therapy belt 100 (hereinafter invention) is a therapeutic device. The invention 100 is configured for use with a patient 104. The patient 104 is further defined with a torso 151, a spine 152, a pelvis 153, an abdomen 154, and a lumbar region 155. The invention 100 is adapted to laterally move muscles so as to relieve downward pressure on the spinal discs and nerves of the lumbar region 155. The patient 104 is defined elsewhere in this disclosure. The torso 151, the spine 152, the pelvis 153, the abdomen 154, and the lumbar region 155 are defined elsewhere in this disclosure.

The invention 100 comprises a belt 101, a fastener 102, and a plurality of pads 103. The fastener 102 and the plurality of pads 103 attach to the belt 101. The belt 101 is a strap. The fastener 102 attaches the belt 101 to the patient 104 such that the plurality of pads 103 are positioned over the lumbar region 155. The plurality of pads 103 press against the lumbar region 155 such that the normal movement of the patient 104 causes the plurality of pads 103 to move muscles laterally so as to relieve downward pressure on the spinal discs and nerves of the lumbar region 155, including spinal muscles, in a fashion similar to the kneading motion.

The belt 101 is a disk-shaped strap of a flexible material. The belt 101 is a roughly rectangular sheeting structure. The fastener 102 and the plurality of pads 103 attach to the belt 101. The belt 101 wraps around the abdomen 154 and the lumbar region 155 of the patient 104. The belt 101 is worn by the patient 104 such that the plurality of pads 103 are positioned over the lumbar region 155 of the patient 104. The applicant prefers that the belt 101 is formed from a material selected from the group consisting of a textile webbing or leather. The belt 101 further comprises a first end 111, a second end 112, an exterior face 113, and an interior face 114.

The first end 111 is the edge of the roughly rectangular shape of the belt 101 with the least span of length. The second end 112 is the edge of the roughly rectangular shape of the belt 101 that is distal from the first end 111. The exterior face 113 is the face of the belt 101 with the greatest surface area. The exterior face 113 is the face of the belt 101 that is distal from the skin of the patient 104 when the belt 101 is worn as intended. The interior face 114 is the face of the belt 101 that is distal from the skin of the exterior face 113. The interior face 114 is the face of the belt 101 that is proximal to the skin of the patient 104 when the belt 101 is worn as intended.

The fastener 102 is a fastening device. The fastener 102 attaches the belt 101 to itself such that the belt 101 forms a loop around the abdomen 154 and the lumbar region 155 of the patient 104. Specifically, the fastener 102 attaches the first end 111 of the belt 101 to the second end 112 of the belt 101 such that the first end 111 and the second end 112 overlap. The fastener 102 secures the belt 101 to the patient 104 such that the plurality of pads 103 are pressed into the lumbar region 155 of the patient 104. The fastener 102 controls the tension applied to the belt 101 and thereby the pressure applied to the plurality of pads 103.

In the first potential embodiment of the disclosure, the fastener 102 is a hook and loop fastener. The fastener 102 comprises a first hook/loop surface 121 and a second hook/loop surface 122.

The first hook/loop surface 121 is the first element of the hook and loop fastener that forms the fastener 102. The first hook/loop surface 121 attaches to the exterior face 113 of the belt 101 at a location proximal to the first end 111 of the belt 101. The second hook/loop surface 122 is the second element of the hook and loop fastener that forms the fastener 102. The second hook/loop surface 122 attaches to the interior face 114 of the belt 101 at a location proximal to the second end 112 of the belt 101.

The first hook/loop surface 121 presses against the second hook/loop surface 122 to attach the belt 101 to itself to secure the belt 101 to the patient 104. The tension applied to the plurality of pads 103 by the belt 101 is controlled by controlling the position of the first hook/loop surface 121 relative to the second hook/loop surface 122 before attaching the first hook/loop surface 121 to the second hook/loop surface 122.

The hook and loop fastener and the hook/loop surface is defined in greater detail elsewhere in this disclosure.

Each of the plurality of pads 103 is an elastomeric structure. Each of the plurality of pads 103 forms a pad that is pressed into the lumbar region 155 of the patient 104 by the tension on the belt 101. Each of the plurality of pads 103 remains in a roughly stationary position while pressed against the lumbar region 155 of the patient 104. During normal activity, the movement of the patient 104 causes the lumbar region 155 to move relative to the plurality of pads 103. This movement of the lumbar region 155 relative to the roughly stationary position of the plurality of pads 103 causes the muscles of the lumbar region 155 to stretch muscles laterally so as to relieve downward pressure on the spinal discs and nerves. The plurality of pads 103 comprises a first pad 131 and a second pad 141.

The first pad 131 is a roughly rectangular structure. The first pad 131 is an elastomeric structure. The first pad 131 is a readily and commercially available structure that is commonly marketed using a term selected from the group consisting of a gel pad and a hydrogel pad. The first pad 131 attaches to the interior face 114 of the belt 101. The first pad 131 presses against the lumbar region 155 of the patient 104 when the invention 100 is worn as intended. The pressure applied by the first pad 131 is determined by the tension applied to the belt 101 by the fastener 102. The first pad 131 is further defined with a modulus. The modulus of the first pad 131 is selected such that the first pad 131 will not shift significantly during the normal activities of the patient 104.

The first pad 131 further comprises a first attachment disk 132 and a first hyoid clip 133.

The first attachment disk 132 is a disk-shaped structure that attaches to the exterior surface of the first pad 131. The first attachment disk 132 attaches the first pad 131 to the first hyoid clip 133. The first hyoid clip 133 is a cantilever V spring. The first hyoid clip 133 is a hyoid-shaped structure. The first hyoid clip 133 is a semi-rigid structure with an elastomeric nature. The first hyoid clip 133 is a clip that attaches to the interior face 114 of the belt 101. The first hyoid clip 133 removably attaches the first pad 131 to the belt 101 such that the first pad 131 is positioned over the lumbar region 155 of the patient 104.

The first hyoid clip 133 is formed with a track that is sized to receive the lateral face of the first attachment disk 132. The lateral face of the first attachment disk 132 inserts into the track of the first hyoid clip 133 to secure the first attachment disk 132 to the first hyoid clip 133.

The first hyoid clip 133 acts as a spring. Specifically, when the first attachment disk 132 inserts between the first arm and the second arm of the hyoid structure of the first hyoid clip 133 which creates a force that separates the first arm from the second arm. The elasticity of the first hyoid clip 133 creates a force that opposes the displacement created force created by the insertion of the first attachment disk 132. The displacing force places a strain on the first hyoid clip 133 creating an opposing force within the first hyoid clip 133 such that the opposing force of the strain is in the direction that returns the first hyoid clip 133 to its relaxed shape. This spring-like action produces a clamping force that can be used to hold the first attachment disk 132 within the first hyoid clip 133 and thereby attach the first pad 131 to the belt 101.

The second pad 141 is a roughly rectangular structure. The second pad 141 is an elastomeric structure. The second pad 141 is a readily and commercially available structure that is commonly marketed using a term selected from the group consisting of a gel pad and a hydrogel pad. The second pad 141 attaches to the interior face 114 of the belt 101. The second pad 141 presses against the lumbar region 155 of the patient 104 when the invention 100 is worn as intended. The pressure applied by the second pad 141 is determined by the tension applied to the belt 101 by the fastener 102. The second pad 141 is further defined with a modulus. The modulus of the second pad 141 is selected such that the second pad 141 will not shift significantly during the normal activities of the patient 104.

The second pad 141 further comprises a second attachment disk 142 and a second hyoid clip 143.

The second attachment disk 142 is a disk-shaped structure that attaches to the exterior surface of the second pad 141. The second attachment disk 142 attaches the second pad 141 to the second hyoid clip 143.

The second hyoid clip 143 is a cantilever V spring. The second hyoid clip 143 is a hyoid-shaped structure. The second hyoid clip 143 is a semi-rigid structure with an elastomeric nature. The second hyoid clip 143 is a clip that attaches to the interior face 114 of the belt 101. The second hyoid clip removably attaches the second pad 141 to the belt 101 such that the second pad 141 is positioned over the lumbar region 155 of the patient 104.

The second hyoid clip 143 is formed with a track that is sized to receive the lateral face of the second attachment disk 142. The lateral face of the second attachment disk 142 inserts into the track of the second hyoid clip 143 to secure the second attachment disk 142 to the second hyoid clip 143.

The second hyoid clip 143 acts as a spring. Specifically, the second attachment disk 142 inserts between the first arm and the second arm of the hyoid structure of the second hyoid clip 143 which creates a force that separates the first arm from the second arm. The elasticity of the second hyoid clip 143 creates a force that opposes the displacement created force created by the insertion of the second attachment disk 142. The displacing force places a strain on the second hyoid clip 143 creating an opposing force within the second hyoid clip 143 such that the opposing force of the strain is in the direction that returns the second hyoid clip 143 to its relaxed shape. This spring-like action produces a clamping force that can be used to hold the second attachment disk 142 within the second hyoid clip 143 and thereby attach the second pad 141 to the belt 101.

The following definitions were used in this disclosure:

Abdomen: As used in this disclosure, the abdomen refers to the portion of the torso between the bottom of the rib cage and the hips of the person.

Cantilever: As used in this disclosure, a cantilever is a beam or other structure that projects away from an object and is supported on only one end. A cantilever is further defined with a fixed end and a free end. The fixed end is the end of the cantilever that is attached to the object. The free end is the end of the cantilever that is distal from the fixed end.

Cantilever V Spring: As used in this disclosure, a cantilever V spring is a torsion spring that is formed in a chevron, hyoid or horseshoe shape. The cantilever V spring comprises a first cantilever structure and a second cantilever structure wherein the fixed end of the first cantilever structure is attached to the fixed end of the second cantilever structure. Within this structure, when a force is applied to the cantilever V spring such that the first cantilever structure moves relative to from the second cantilever structure the force deforms the cantilever V spring in an elastic manner that: 1) resists the application of the force; and 2) stores the energy deformation such that when the force is no longer applied the cantilever V spring returns to its relaxed shape. Depending on the application, a cantilever V spring can be considered a torsion spring, a tension spring, or a compression spring. The term offset cantilever V spring means that the span of the length of the first cantilever structure differs from the span of the length of the second cantilever structure.

Clip: As used in this disclosure, a clip is a fastener that attaches to an object by gripping or clasping the object. A clip is typically spring loaded.

Disk: As used in this disclosure, a disk is a prism-shaped object that is flat in appearance. The disk is formed from two congruent ends that are attached by a lateral face. The sum of the surface areas of two congruent ends of the prism-shaped object that forms the disk is greater than the surface area of the lateral face of the prism-shaped object that forms the disk. In this disclosure, the congruent ends of the prism-shaped structure that forms the disk are referred to as the faces of the disk.

Elastic: As used in this disclosure, an elastic is a material or object that deforms when a force is applied to it and that is able to return to its relaxed shape after the force is removed. A material that exhibits these qualities is also referred to as an elastomeric material. A material that does not exhibit these qualities is referred to as inelastic or an inelastic material.

Fastener: As used in this disclosure, a fastener is a device that is used to join or affix two objects. Fasteners generally comprise a first element which is attached to the first object and a second element which is attached to the second object such that the first element and the second element join to removably attach the first object and the second object. Common fasteners include, but are not limited to, hooks, zippers, magnets, snaps, buttons, buckles, quick release buckles, or hook and loop fasteners.

Gel: As used in this disclosure, a gel is a substance comprising mostly of liquid (by mass) that is trapped in a cross-linked network structure that exhibits the properties of an elastic solid.

Hook and Loop Fastener: As used in this disclosure, a hook and loop fastener is a fastener that comprises a hook surface and a loop surface. The hook surface comprises a plurality of minute hooks. The loop surface comprises a surface of uncut pile that acts like a plurality of loops. When the hook surface is applied to the loop surface, the plurality of minute hooks fastens to the plurality of loops securely fastening the hook surface to the loop surface. A note on usage: when fastening two objects the hook surface of a hook and loop fastener will be placed on the first object and the matching loop surface of a hook and loop fastener will be placed on the second object without significant regard to which object of the two objects is the first object and which of the two objects is the second object. When the hook surface of a hook and loop fastener or the loop surface of a hook and loop fastener is attached to an object this will simply be referred to as the "hook/loop surface" with the understanding that when the two objects are fastened together one of the two objects will have a hook surface and the remaining object will have the loop surface.

Hyoid: As used in this disclosure, a hyoid refers to a three-sided structure comprising a crossbeam, a first arm, and a second arm. In a hyoid, the first arm and the second arm project away from the crossbeam: 1) in the same direction; 2) at a roughly perpendicular angle to the crossbeam, and, 3) the span of the length of the first arm roughly equals the span of the length of the second arm. Hyoids generally have a U shaped appearance.

Loop: As used in this disclosure, a loop is the length of a first linear structure including, but not limited to, shafts, lines, cords, or webbings, that is: 1) folded over and joined at the ends forming an enclosed space; or, 2) curved to form a closed or nearly closed space within the first linear structure. In both cases, the space formed within the first linear structure is such that a second linear structure such as a line, cord or a hook can be inserted through the space formed within the first linear structure. Within this disclosure, the first linear structure is said to be looped around the second linear structure.

Lumbar: As used in this disclosure, the lumbar refers to the lower back region of a person. Depending on the context, the lumbar region is either: 1) adjacent to the loin region of a person; or, 2) incorporates the upper portion of the loin region of a person.

Modulus: As used in this disclosure, the modulus of an elastomeric structure is a function that describes the resistance to the deformation of the elastomeric structure as a function of the force applied to the elastomeric structure. When comparing modulus, a larger modulus is taken to imply a greater force is required to achieve the same deformation.

Not Significantly Different: As used in this disclosure, the term not significantly different compares a specified property of a first object to the corresponding property of a reference object (reference property). The specified property is considered to be not significantly different from the reference property when the absolute value of the difference between the specified property and the reference property is less than 10.0% of the reference property value. A negligible difference is considered to be not significantly different. See negligible difference.

Pad: As used in this disclosure, a pad is a mass of soft material used as a filling or for protection against damage or injury. Commonly used padding materials include, but are not limited to, polyurethane foam, silicone, gels, a polyester fill often referred to as fiberfill or polystyrene beads often referred to as stuffing beans or as bean bag chair beans.

Patient: As used in this disclosure, a patient is a person who is designated to receive a medical treatment, therapy or service. The term patient may be extended to an animal when used within the context of the animal receiving veterinary treatment or services.

Pelvis: As used in this disclosure, the pelvis refers to a bone structure near the base of the spine to which buttocks and the legs are joined. As used in this disclosure, the term pelvis is more generally expanded to describe the above-described region of the body. As used in this disclosure, the adjectival form of pelvis is pelvic.

Prism: As used in this disclosure, a prism is a three-dimensional geometric structure wherein: 1) the form factor of two faces of the prism are congruent; and, 2) the two congruent faces are parallel to each other. The two congruent faces are also commonly referred to as the ends of the prism. The surfaces that connect the two congruent faces are called the lateral faces. In this disclosure, when further description is required a prism will be named for the geometric or descriptive name of the form factor of the two congruent faces. If the form factor of the two corresponding faces has no clearly established or well-known geometric or descriptive name, the term irregular prism will be used. The center axis of a prism is defined as a line that joins the center point of the first congruent face of the prism to the center point of the second corresponding congruent face of the prism. The center axis of a prism is otherwise analogous to the center axis of a cylinder. A prism wherein the ends are circles is commonly referred to as a cylinder.

Relaxed Shape: As used in this disclosure, a structure is considered to be in its relaxed state when no shear, strain, or torsional forces are being applied to the structure.

Roughly: As used in this disclosure, roughly refers to a comparison between two objects. Roughly means that the difference between one or more parameters of the two compared are not significantly different.

Semi-Rigid Structure: As used in this disclosure, a semi-rigid structure is a solid structure that is stiff but not wholly inflexible and that will deform under force before breaking. A semi-rigid structure may or may not behave with an elastic nature in that a semi-rigid structure need not return to its relaxed shape.

Sheeting: As used in this disclosure, a sheeting is a material, such as a paper, textile, a plastic, or a metal foil, in the form of a thin flexible layer or layers.

Spine: As used in this disclosure, the spine of a human being comprises 33 individual bones that are formed in a column structure. The spine commonly referred to as the back bone. The spine is divided into five regions which are, in order from head to buttocks, the cervical region, the thoracic region, the lumbar region, the sacral region, and the coccyx region.

Spine Muscle: As used in this disclosure, a spine muscle is a muscle that is attached to the spine.

Spring: As used in this disclosure, a spring is a device that is used to store mechanical energy. This mechanical energy will often be stored by: 1) deforming an elastomeric material that is used to make the device; 2) the application of a torque to a semi-rigid structure; or 3) a combination of the previous two items.

Strap: As used in this disclosure a strap is a strip of leather, cloth, or other flexible material, often with a buckle, that is used to fasten, secure, carry, or hold onto something.

Strip: As used in this disclosure, the term describes a long and narrow object of uniform thickness that appears thin relative to the length of the object. Strips are often rectangular in shape.

Textile: As used in this disclosure, a textile is a material that is woven, knitted, braided or felted. Synonyms in common usage for this definition include fabric and cloth.

Therapeutic: As used in this disclosure, therapeutic is an adjective that refers to a medical, ameliorative, or hygienic substance, process, or procedure.

Torso: As used in this disclosure, the torso refers to the portion of a human body between the neck and the pelvis. The spine is primarily contained within the torso.

Track: As used in this disclosure, a track is a structural relationship between a first object and a second object that serves a purpose selected from the group consisting of: 1) fastening the second object to the first object; 2) controlling the path of motion of the first object relative to the second object in at least one dimension and in a maximum of two dimensions; or, 3) a combination of the first two elements of this group.

Webbing: As used in this disclosure, a webbing is strong, close woven or knitted fabric that is used for straps or belting. As used in this disclosure, webbing is a fully formed material that is only cut to length for use. Webbing is not formed by cutting broader materials into strips. Webbings have tensile strength but are too flexible to provide compressive strength and are not suitable for use in pushing objects. The two surfaces of a webbing with the greatest surface area are called the faces of the webbing.

With respect to the above description, it is to be realized that the optimum dimensional relationship for the various components of the invention described above and in FIGS. 1 through 4 include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

The inventor claims:
1. A lumbar therapy belt comprising
a belt, a fastener, and a plurality of pads;
wherein the fastener and the plurality of pads attach to the belt; wherein the lumbar therapy belt is a therapeutic device;
wherein the lumbar therapy belt is configured for use with a patient;
wherein the lumbar therapy belt is adapted to move muscles of the lumbar region of the patient laterally so as to relieve downward pressure on the spinal discs and nerves;
wherein the belt further comprises a first end, a second end, an exterior face, and an interior face; wherein the plurality of pads comprises a first pad and a second pad;
wherein the first pad further comprises a first attachment disk and a first hyoid clip;
wherein the second pad further comprises a second attachment disk and a second hyoid clip;
wherein the first hyoid clip is a cantilever V spring;
wherein the first hyoid clip is a hyoid-shaped structure;
wherein the first hyoid clip is a semi-rigid structure with an elastomeric nature;
wherein the first hyoid clip is a clip that attaches to the interior face of the belt;
wherein the first attachment disk inserts into the first hyoid clip to secure the first attachment disk to the first hyoid clip;
wherein the second hyoid clip is a cantilever V spring;
wherein the second hyoid clip is a hyoid-shaped structure;
wherein the second hyoid clip is a semi-rigid structure with an elastomeric nature;
wherein the second hyoid clip is a clip that attaches to the interior face of the belt;
wherein the second attachment disk inserts into the second hyoid clip to secure the second attachment disk to the second hyoid clip.
2. The lumbar therapy belt according to claim 1 wherein the belt is a strap; wherein the fastener is configured to attach the belt to the patient such that the plurality of pads are positioned over the lumbar region.
3. The lumbar therapy belt according to claim 2
wherein the belt is a disk-shaped strap of a flexible material;
wherein the belt is a roughly rectangular sheeting structure;
wherein the belt wraps around the abdomen and the lumbar region of the patient.
4. The lumbar therapy belt according to claim 3
wherein the fastener is a fastening device;
wherein the fastener attaches the belt to itself such that the belt forms a loop around the abdomen and the lumbar region of the patient.
5. The lumbar therapy belt according to claim 4
wherein the fastener attaches the first end of the belt to the second end of the belt such that the first end and the second end overlap;
wherein the fastener secures the belt to the patient such that the plurality of pads are pressed into the lumbar region of the patient.
6. The lumbar therapy belt according to claim 5 wherein the fastener controls a tension applied to the belt.
7. The lumbar therapy belt according to claim 6 wherein each of the plurality of pads is an elastomeric structure.

8. The lumbar therapy belt according to claim 7
wherein each of the plurality of pads forms a pad that is pressed into the lumbar region of the patient by the tension on the belt;
wherein each of the plurality of pads remains in a roughly stationary position while pressed against the lumbar region of the patient;
wherein the movement of the patient causes the lumbar region to move relative to the plurality of pads;
wherein this movement of the lumbar region relative to the roughly stationary position of the plurality of pads is adapted to cause the muscles of the lumbar region to stretch.
9. The lumbar therapy belt according to claim 8
wherein the first pad attaches to the interior face of the belt;
wherein the second pad attaches to the interior face of the belt.
10. The lumbar therapy belt according to claim 9
wherein the first pad is a roughly rectangular structure;
wherein the first pad is an elastomeric structure;
wherein the first pad is further defined with a modulus;
wherein the second pad is a roughly rectangular structure;
wherein the second pad is an elastomeric structure;
wherein the second pad is further defined with a modulus;
wherein the second pad attaches to the interior face of the belt.
11. The lumbar therapy belt according to claim 10
wherein the first pad is adapted to press against the lumbar region of the patient;
wherein the pressure applied by the first pad is determined by the tension applied to the belt by the fastener;
wherein the modulus of the first pad is selected such that the first pad is adapted to not shift on the patient;
wherein the second pad is adapted to press against the lumbar region of the patient;
wherein the pressure applied by the second pad is determined by the tension applied to the belt by the fastener;
wherein the modulus of the second pad is selected such that the second pad is adapted to not shift on the patient.
12. The lumbar therapy belt according to claim 11
wherein the first attachment disk attaches the first pad to the first hyoid clip;
wherein the second attachment disk attaches the second pad to the second hyoid clip.
13. The lumbar therapy belt according to claim 12
wherein the first attachment disk is a disk-shaped structure that attaches to the exterior surface of the first pad;
wherein the second attachment disk is a disk-shaped structure that attaches to the exterior surface of the second pad.
14. The lumbar therapy belt according to claim 13 wherein the fastener is a hook and loop fastener.
15. The lumbar therapy belt according to claim 14
wherein the fastener comprises a first hook/loop surface and a second hook/loop surface;
wherein the first hook/loop surface is a first element of the hook and loop fastener that forms the fastener;
wherein the second hook/loop surface is a second element of the hook and loop fastener that forms the fastener.
16. The lumbar therapy belt according to claim 15
wherein the first hook/loop surface attaches to the exterior face of the belt at a location proximal to the first end of the belt;
wherein the second hook/loop surface attaches to the interior face of the belt at a location proximal to the second end of the belt.

17. The lumbar therapy belt according to claim 16 wherein the first hook/loop surface presses against the second hook/loop surface to attach the belt to itself to secure the belt to the patient.

18. The lumbar therapy belt according to claim 17 wherein the tension applied to the plurality of pads by the belt is controlled by controlling the position of the first hook/loop surface relative to the second hook/loop surface before attaching the first hook/loop surface to the second hook/loop surface.

19. The lumbar therapy belt according to claim 18 wherein the belt is formed from a material selected from the group consisting of a textile webbing or leather.

* * * * *